United States Patent [19]

Kwon et al.

[11] 4,126,526
[45] Nov. 21, 1978

[54] CYCLIC PROCESS FOR PRODUCTION OF ALKYLENE OXIDE USING ELECTROLYSIS OF BRINE

[75] Inventors: Joon T. Kwon, Freehold Township, Monmouth County; Abraham P. Gelbein, Plainfield, both of N.J.

[73] Assignee: The Lummus Company, Bloomfield, N.J.

[21] Appl. No.: 851,853

[22] Filed: Nov. 16, 1977

[51] Int. Cl.² .............. C25B 1/34; C07D 301/00; C07C 29/00; C07C 31/34
[52] U.S. Cl. .............................. 204/98; 204/80; 260/348.21; 260/348.22; 260/453 R X
[58] Field of Search ............ 204/80, 98, 128; 260/348.21, 348.22, 453 R

[56] References Cited

U.S. PATENT DOCUMENTS

| | | | |
|---|---|---|---|
| 3,149,140 | 9/1964 | Nevin | 260/453 R X |
| 3,288,692 | 11/1966 | Leduc | 204/80 |
| 3,455,797 | 7/1969 | Courtier | 204/80 |
| 3,617,581 | 11/1971 | Wang et al. | 210/62 |
| 3,894,059 | 7/1975 | Selvaratnam et al. | 260/348.21 |
| 4,008,133 | 2/1977 | Gelbein et al. | 204/80 |

FOREIGN PATENT DOCUMENTS

| | | | |
|---|---|---|---|
| 1,295,535 | 5/1969 | Fed. Rep. of Germany | 260/348.21 |
| 2,144,084 | 2/1973 | France | 260/348.21 |

*Primary Examiner*—F.C. Edmundson
*Attorney, Agent, or Firm*—Marn & Jangarathis

[57] ABSTRACT

In an integrated process for electrolytic production of chlorine and the production of an olefin oxide via the chlorohydrin wherein the chlorohydrin is contacted with an aqueous solution of sodium hydroxide and sodium chloride from the cathode compartment of an electrolytic cell, to produce the oxide and brine, the brine is contacted with gaseous chlorine to oxidize organic impurities to volatile organic fragments, which are stripped from the brine, prior to recycling the brine to the electrolytic cell.

12 Claims, 1 Drawing Figure

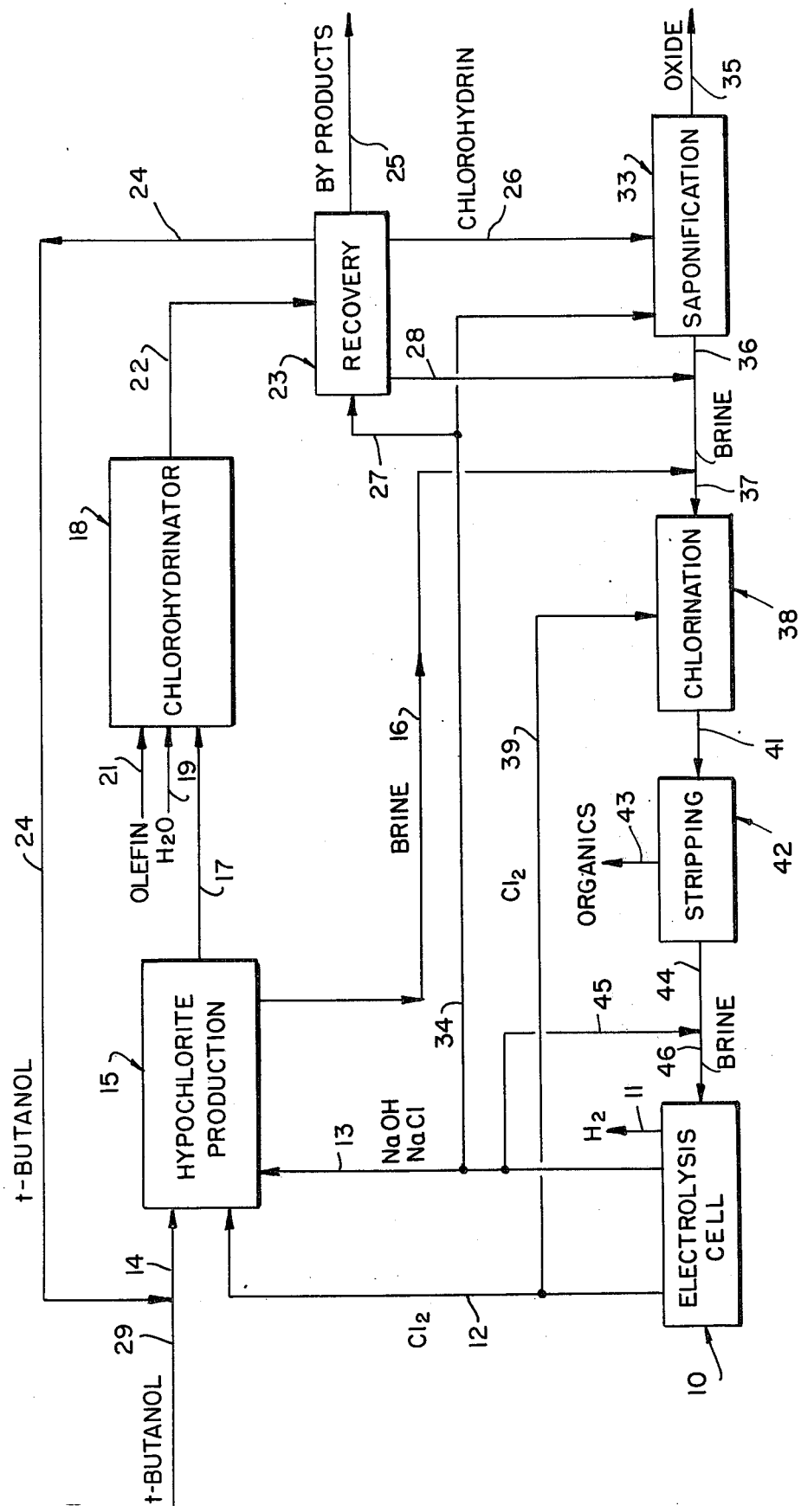

CYCLIC PROCESS FOR PRODUCTION OF ALKYLENE OXIDE USING ELECTROLYSIS OF BRINE

This invention relates to the production of epoxy compounds, and more particularly, to a new and improved process for producing epoxy compounds from olefinically unsaturated compounds, via the chlorohydrin route.

In U.S. Pat. No. 3,455,797, there is described a process for producing olefin oxides wherein chlorine generated in an electrolytic cell is employed for converting an olefin to the corresponding chlorohydrin. The resulting chlorohydrin is then converted to the oxide by saponification in an aqueous solution of sodium chloride and sodium hydroxide recovered from the cathode compartment of the cell. Brine recovered from the saponification is recycled to the electrolytic cell.

In U.S. Pat. No. 4,008,133, there is described a process for producing an olefin oxide via the chlorohydrin route wherein chlorine generated in an electrolytic cell is employed to convert a tertiary alkanol to a tertiary alkyl hypochlorite, with the hypochlorite then being reacted with an olefin to produce the chlorohydrin. The chlorohydrin is then saponified with aqueous sodium chloride and sodium hydroxide recovered from the electrolytic cell, with brine generated in the saponification being recycled to the cell.

The present invention is directed to an improvement in a process for producing an epoxy compound via the chlorohydrin route which is integrated with an electrolytic process for producing chlorine.

In accordance with the present invention wherein an electrolytic process for producing chlorine is combined with a chlorohydrin process for producing an epoxy compound, the chlorohydrin is saponified to the epoxy compound by contact with an aqueous solution of sodium chloride and sodium hydroxide recovered from the cathode compartment of the chlorine producing electrolytic cell. An aqueous brine solution, containing organic impurities, is recovered from the saponification and directly contacted with gaseous chlorine to oxidize the organic impurities to volatile fragments. The volatile fragments are stripped from the aqueous brine solution, and the aqueous brine solution is returned to the electrolytic cell. Applicant has found that the electrolytic cells cannot tolerate organic compounds above a certain level, and in accordance with the present invention the organic content of the recycle brine is reduced to below such tolerance levels prior to introduction into the electrolytic cell.

More particularly, the aqueous brine solution, containing organic impurities, is contacted with gaseous chlorine at conditions effective for oxidizing the organic impurities to volatile fragments. More particularly, the aqueous brine solution, containing organic impurities, is contacted with gaseous chlorine at a temperature in the order of from about 120° to about 240° F. and preferably at a temperature of from about 140° F. to 220° F. It is to be understood, however, that such temperatures are merely illustrative, and the use of other temperatures is deemed to be within the scope of those skilled in the art from the teachings herein.

The chlorine is employed in an amount less than that required to oxidize all of the organic impurities to carbon dioxide and water. Applicant found that the chlorine can be employed in less than such stoichiometric proportions in that the chlorine could be employed to oxidize the organic impurity to more volatile partial oxidation fragments which could then be stripped from the aqueous brine solution. Thus, the organic impurities are converted to volatile organic compounds whereby organic impurities are removed from the recycle brine at reduced chlorine consumption. In general, the chlorine is employed in an amount which is no greater than 80% of the stoichiometric requirements for converting the organic impurities to carbon dioxide, and preferably no greater than 65%. The selection of an optimum amount of chlorine for converting the organic impurities to volatile organic compounds is deemed to be within the scope of those skilled in the art from the teachings herein.

The particular organic impurities present in the brine solution treated in accordance with the present invention is dependent upon the olefinically unsaturated compound employed as starting material. In general, such organic impurities are glycols, aldehydes and ethers. The treatment with chlorine, as hereinabove described, is effected to convert the organic impurities to more volatile organic fragments and in general, such treatment is effected to provide organic compound having a boiling point no greater than 150° C., and preferably not in excess of 120° C.

The olefinically unsaturated compound employed as feed in the present process may be any one of a wide variety of olefinically unsaturated compounds, including both mono-olefinically and di-olefinically unsaturated compounds. The olefinically unsaturated compounds generally employed as feed are represented by the following structural formula:

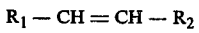

$$R_1 - CH = CH - R_2$$

wherein $R_1$ and $R_2$ are each separately either hydrogen; alkyl; halo alkyl; phenyl; naphthyl; halo-and alkyl substituted phenyl; halo-and alkyl substituted naphthyl; alkenyl and halo substituted alkenyl; and $R_1$ and $R_2$ can be linked together to provide a cycloalkene (generally 5 to 10 carbon atoms). The alkyl and alkenyl groups generally contain 1 to 6 carbon atoms and the halo group is preferably iodo-, bromo-, or chloro-, most preferably chloro-. As representative examples of the most suitable feedstocks, there may be mentioned: alkenes having from 2 to 6 carbon atoms, preferably 2 to 4 carbon atoms with ethylene and propylene being particularly preferred; styrene; stilbene; butadiene; chloroprene; allyl chloride; allyl bromide; bromoprene; cyclohexene, and cyclopentene. The epoxy compounds generally produced in accordance with the invention are represented by the following structural formula:

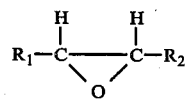

wherein $R_1$ and $R_2$ are as defined above.

The present invention is particularly applicable to a process for producing epoxy compounds from olefinic compounds, as described in U.S. Pat. No. 4,008,133. In accordance with such a process, chlorine produced in the electrolytic cell is introduced into a hypochlorite production reaction zone, wherein the chlorine is reacted with a tertiary alkanol, preferably a tertiary alkanol having from 4 to 6 carbon atoms, and most preferably tertiary butanol or tertiary amyl alcohol and sodium hydroxide in an aqueous brine solution, obtained from the electrolytic cell, as represented by the following equations:

$$Cl_2 + 2 NaOH \rightarrow NaOCl + NaCl + H_2O$$

$$NaOCl + ROH \rightarrow ROCl + NaOH$$

$$Cl_2 + NaOH + ROH \rightarrow ROCl + NaCl + H_2O$$

The specific conditions employed for the production of the hypochlorite are more fully described in the aforesaid patent, which is hereby incorporated via reference.

In accordance with the present invention, the aqueous brine solution generated in the hypochlorite production reaction, which contains some organic impurities; namely, the tertiary alkanol and hypochlorite, is treated with chlorine to convert the organic impurities to more volatile organic fragments, which can be stripped from the brine solution.

The organic phase, recovered from the hypochlorite production reactor, is then introduced into a chlorohydrin production reactor, wherein the tertiary alkyl hypochlorite is contacted with an olefinically unsaturated compound and water, which is essentially free of chloride ion to produce the chlorohydrin, as represented by the following equation using propylene as a representative olefin:

$$ROCl + H_2O + C_3H_6 \rightarrow ROH + C_3H_7OCl$$

The details with respect to the production of the chlorohydrin is described in more detail in U.S. Pat. No. 4,008,133, which is hereby incorporated by reference.

The chlorohydrin recovered from the chlorohydrinator is then introduced into a saponifier wherein the chlorohydrin is dehydrochlorinated to produce the corresponding epoxy compound by the use of liquor obtained from the cathode compartment of the electrolytic cell which contains sodium hydroxide and sodium chloride. The chlorohydrin reacts with the sodium hydroxide to produce the epoxy and an aqueous brine, as represented by the following equation, using propylene chlorohydrin as a representative example:

$$C_3H_7OCl + NaOH \rightarrow C_3H_6O + NaCl + H_2O$$

The details of the saponification reaction are described in U.S. Pat. No. 4,008,133.

The epoxy compound is recovered as a reaction product from the saponification zone, and the aqueous brine recovered from the saponification zone is treated with chlorine, as hereinabove described, to convert organic impurities to more volatile fractions which are stripped from the brine solution, prior to introduction thereof into the electrolytic cell.

In accordance with the preferred embodiment, the chlorine treatment is effected on a recycle brine which includes both glycol and tertiary alkanol in the organic impurities. The glycol impurity is generally present in the brine recovered from the saponification reactor and the tertiary alkanol impurity is generally present in the brine recovered from the hypochlorite production reactor, although as should be apparent some tertiary alkanol may also be present in the brine recovered from the saponification reactor. Applicant has found that when a recycle brine which includes both tertiary alkanol and glycol is treated with chlorine the organic impurities can be converted to volatile organic compounds at reduced chlorine consumption. As a result, it is preferred to combine recycle brine recovered from both the hypochlorite production reactor and the saponifier for chlorine treatment to convert the organic impurities to strippable organic compounds for removal from the recycle brine.

The present invention will be further described with respect to an embodiment thereof illustrated in the accompanying drawing:

The drawing is a simplified schematic flow diagram of an embodiment of the present invention.

It is to be understood, however, that the scope of the invention is not limited to such an embodiment.

Referring now to the drawing, there is shown an electrolytic cell 10, of a type known in the art, wherein, as known in the art, hydrogen is produced at the cathode, and chlorine at the anode, using sodium chloride as electrolyte. The hydrogen is withdrawn from the cell as net product, through line 11.

Chlorine produced in cell 10 is withdrawn therefrom through line 12 and introduced into a hypochlorite production reaction zone, along with cell liquor in line 13, containing sodium hydroxide and sodium chloride, which is obtained from the cathode compartment of cell 10. Recycle tertiary alkanol, in particular, tertiary butyl alcohol in line 14 is also introduced into the hypochlorite production reactor schematically generally indicated as 15.

In reactor 15, the tertiary butyl alcohol, chlorine and cell liquor are reacted to produce tertiary butyl hypochlorite, and an aqueous brine solution.

An aqueous brine solution, containing organic impurities, is withdrawn from reactor 15 through line 16 for further treatment, as hereinafter described.

An organic phase, containing the hypochlorite, is withdrawn from reactor 15 through line 17 and introduced into a chlorohydrin production reactor schematically generally indicated as 18. Water, essentially free of chloride ion, and olefin; in particular, propylene, are introduced into reactor 18 through lines 19 and 21 respectively. In reactor 18, the hypochlorite, water and olefin are reacted to produce, as co-reaction products, propylene chlorohydrin and tertiary butyl alcohol.

A chlorohydrin production effluent, containing propylene chlorohydrin, water, tertiary butyl alcohol, and organic byproducts is withdrawn from reactor 18 through line 22 and introduced into a separation and recovery zone, schematically indicated as 23. The separation and recovery zone 23 contains appropriate separation units to recover recycle tertiary butanol in line 24, organic byproducts through line 25 and a chlorohydrin containing stream through line 26. A representative separation and recovery operation is described in U.S. Pat. No. 4,008,133.

Cell liquor from the cathode compartment of the electrolytic cell, which contains sodium hydroxide and sodium chloride, may also be introduced into the separation and recovery zone 23 through line 27 in order to neutralize any hydrogen chloride present in the chlorohydrin production effluent. In such a case, an aqueous brine solution is also recovered through line 28 for treatment as hereinafter described.

The tertiary butanol in line 24, is combined with make up tertiary butanol in line 29 for introduction into the hypochlorite production reactor 15 through line 14.

The chlorohydrin containing stream in line 26, which is generally a chlorohydrin-water azeotrope is introduced into the saponification reaction zone, generally indicated as 33, along with cell liquor in line 34, containing sodium chloride and sodium hydroxide, which is obtained from the cathode compartment of cell 10. In the saponification reactor, the propylene chlorohydrin is converted to propylene oxide, with the propylene oxide being recovered through line 35, as reaction product.

An aqueous brine solution, containing some organic impurities is withdrawn from the saponification reaction zone 33 through line 36 combined with the brine solutions in line 16 and 28, and the combined stream in line 37 introduced into a chlorination reaction zone, schematically indicated as 38. The chlorine reaction zone 38 is provided with chlorine obtained from the electrolytic cell through line 39.

In chlorinator 38, as hereinabove described, the brine solution, containing organic impurities, is treated with chlorine to effect oxidation of the organic impurities to more volatile organic fragments. The chlorination is effected in a manner such as to produce organic fragments rather than to convert all of the organic impurities to carbon dioxide and water. As hereinabove noted, the treatment is effected to reduce the organic impurities content of the brine to a level below the organic tolerance level of the electrolytic cell by converting the organic impurities to volatile organics which can be stripped from the brine.

An aqueous brine solution, containing more volatile organic impurities, is withdrawn from chlorination reactions zone 38, through line 41, and introduced into a stripping zone, schematically generally indicated as 42, wherein the more volatile organic fragments are stripped from the aqueous brine solution, with such volatile organic fragments being withdrawn through line 43.

An aqueous brine solution free of organic impurities is withdrawn from the stripping zone 42 through line 44, and treated with cell liquor in line 45, obtained from the cathode compartment of the electrolytic cell 10, in order to neutralize the hydrogen chloride generated in the chlorination effected in reactor 38. Neutralized aqueous brine solution is recycled to the electrolytic cell through line 46.

Although the present invention has been desceibed with respect to a preferred embodiment, it should be apparent that the present invention is also applicable to the treatment of brine solutions generated in other processes integrating the electrolytic production of chlorine with the production of an epoxy compound by the chlorohydrin route. Thus, for example, the present invention is also applicable to the treatment of brine solutions generated in an electrolytic process as described in U.S. Pat. No. 3,455,797, or other similar processes.

As a further modification, it is possible, in some cases, to treat only a portion of the recycle brine by chlorination and stripping in order to provide a recycle brine having an organic content below the cell tolerance level.

Similarly, although the embodiment has been described with respect to separate chlorination and stripping operations, the chlorine treatment and stripping may be effected simultaneously; e.g., by feeding in a packed tower, brine countercurrent to ascending chlorine (with or without a diluent gas).

The present invention will be further described with respect to the following example; however, the scope of the invention is not to be limited thereby:

EXAMPLE I 250 cc of simulated recycle brine, containing 1.05 m moles tertiary butanol, 2.55 m miles of sodium hydroxide and 9.50 m moles of propylene glycol is treated with 23.3 m moles of chlorine (all chlorine consumed) at a temperature of 85° C. The treatment brine is then distilled (constant liquor volume by addition of 25 cc water) to strip volatile organics therefrom. The resulting product contained 39.3 m mole of HCl, and as organics 1.84 m mole of propylene glycol; 5 ppm $CH_3CH_2CHO$; 80 ppm $CH_3COCH_3$; 60 ppm $CH_3COOH$; 5 ppm $CH_3CO\ COOH$ 5 ppm $C_2H_5COOH$; 5 ppm ether. The chlorine consumption is 3.04 moles of chlorine per mole of organic converted, which compares to the stoichiometric amount (conversion to carbon dioxide and water) of 9.64 moles of chlorine.

EXAMPLE II 250 cc of simulated recycle brine, containing 3.0 m moles of sodium hydroxide and 8.73 m moles of propylene blycol is treated with 21.1 m moles of chlorine (all chlorine consumed) at a temperature of 85° C. The treated brine is then distilled (constant liquor volume by addition of 25 cc water) to strip volatile organics therefrom. The resulting product contained 36.4 m mole of HCl, and as organics 3.27 m mole of propylene glycol; 5 ppm $CH_3CH_2CHO$; 190 ppm $CH_3CO\ CH_3$ 30 ppm $CH_3COOH$; 0 ppm $CH_3CO\ COOH$; 80 ppm $C_2H_5COOH$; 0 ppm ether. The chlorine consumption is 4.96 moles of chlorine per mole of organic converted, which compares to the stoichiometric amount (conversion to carbon dioxide and water) of 8.0 moles of chlorine.

The present invention is particularly advantageous in that brine can be recycled to the electrolytic cell without adversely affecting the operation thereof as a result of the presence of organic impurities above the cell tolerance level. Moreover, the organic impurities level of the brine is reduced at lower chlorine consumption by effecting chlorination of the brine in combination with stripping whereby the organic impurities are converted to volatile organic compounds which are stripped from the brine. In addition, by treating a brine, which includes in the impurities tertiary alkanol and glycol, (in particular tertiary butanol and propylene glycol) chlorine consumption is further reduced; i.e., chlorine consumed per mole of organic removed from the brine.

These and other advantages should be apparent from the hereinabove description of the present invention.

Numerous modifications and variations of the present invention are possible within the light of the above teachings and therefore, within the scope of the appended claims, the invention may be practiced otherwise than as particularly described.

What is claimed is:

1. In a process integrating an electrolytic process for the production of chlorine with a chlorohydrin process for producing an epoxy compound wherein a chlorohydrin is converted to a corresponding epoxy compound by contact with an aqueous solution of sodium chloride and sodium hydroxide from a chlorine producing electrolytic cell, the improvement comprising:
   recovering an expoxy compound and an aqueous brine solution from the chlorohydrin conversion, said aqueous brine solution containing organic impurities;

contacting said aqueous brine solution with gaseous chlorine to oxidize the organic impurities to move volatile organic compounds;

stripping volatile organic compounds from the aqueous brine solution; and introducing the aqueous brine solution into the electrolytic cell.

2. The process of claim 1 wherein the organic impurities are converted to volatile organic compounds having a boiling point no greater than 150° C.

3. The process of claim 2 wherein the chlorine is employed in an amount less than the stoichiometric amount for converting the organic impurities to carbon dioxide.

4. The process of claim 1 wherein the brine solution is contacted with chlorine at a temperature of from 120° F. to 240° F.

5. The process of claim 1 wherein the contacting and stripping are effected simultaneously.

6. The process of claim 1 wherein the chlorohydrin is propylene chlorohydrin.

7. In a process integrating an electrolytic process for the production of chlorine with a chlorohydrin process for producing an epoxy compound wherein a tertiary alkanol is contacted with gaseous chlorine and an aqueous solution of sodium chloride and sodium hydroxide from an electrolytic cell to produce tertiary alkyl hypochlorite, said hypochlorite is contacted with an olefinically unsaturated compound and water to produce a chlorohydrin, and chlorohydrin is contacted with an aqueous solution of sodium chloride and sodium hydroxide from the electrolytic cell to produce an epoxy compound, the improvement comprising:

recovering a first brine solution from the hypochlorite production, said first brine solution including organic impurities;

recovering a second brine solution from the epoxy production, said second brine solution including organic impurities;

contacting combined first and second brine solution with gaseous chlorine to oxidize organic impurities to more volatile organic compounds;

stripping volatile organic compounds from the combined aqueous brine solution; and introducing combined aqueous brine solution into the electrolytic cell.

8. The process of claim 7 wherein the organic impurities are converted to volatile organic compounds having a boiling point no greater than 150° C.

9. The process of claim 8 wherein the chlorine is employed in an amount less than the stoichiometric amount for converting the organic impurities to carbon dioxide.

10. The process of claim 9 wherein the brine solution is contacted with chlorine at a temperature of from 120° F. to 240° F.

11. The process of claim 10 wherein the olefin is propylene and the organic impurities include tertiary alkanol and propylene glycol.

12. The process of claim 10 wherein the contacting and stripping are effected simultaneously.

* * * * *